US00PP15003P2

(12) United States Plant Patent
Stemkens

(10) Patent No.: US PP15,003 P2
(45) Date of Patent: Jul. 13, 2004

(54) SCAEVOLA PLANT NAMED 'SCAWIHATIS'

(50) Latin Name: *Scaevola aemula*
Varietal Denomination: Scawihatis

(75) Inventor: Henricus G. W. Stemkens, Hoorn (NL)

(73) Assignee: Syngenta Seed BV, Enkhuizen (NL)

( * ) Notice: Subject to any disclaimer, the term of this patent is extended or adjusted under 35 U.S.C. 154(b) by 60 days.

(21) Appl. No.: 10/339,809

(22) Filed: Jan. 10, 2003

(51) Int. Cl.[7] ..... A01H 5/00
(52) U.S. Cl. ..... Plt./363
(58) Field of Search ..... Plt./363

(56) References Cited

U.S. PATENT DOCUMENTS

PP12,027 P2 * 7/2001 Rother ..... Plt./363

OTHER PUBLICATIONS http://www.copf.org/auwa/pdf/PBR%2007–01–03.pdf.* http://www.vkc.nl/UK/registraties/vorigeweek.htm.* http://pss.uvm.edu/ppp/aas2003.htm.*

UPOV ROM GTITM Computer Database, GTI JOUVE Retrieval Software 2003/03 citation(s) for 'Scawihatis'.*

* cited by examiner

*Primary Examiner*—Bruce R. Campell
*Assistant Examiner*—W C Haas
(74) *Attorney, Agent, or Firm*—Bruce Vrana; Edouard G. Lebel

(57) ABSTRACT

A new Scaevola plant named 'Scawihatis', particularly distinguished by its spreading and cascading growth habit and white flowers that have a big light yellow eye.

1 Drawing Sheet

Latin name of the genus and species of the plant claimed: *Scaevola aemula.*
Varietal denomination: 'Scawihatis'.

BACKGROUND OF THE NEW PLANT

The present invention relates to a new and distinct cultivar of Scaevola plant, botanically known as *Scaevola aemula,* synonym *Scaevola saligna* and referred to by the cultivar name 'Scawihatis'.

The new cultivar is a product of a planned breeding program conducted by the Inventor in Enkhuizen, Netherlands. The objective of the breeding program was to create new early Scaevola cultivars.

The new cultivar originated from a cross made in 1999 of two own selections of *Scaevola aemula:* 'A102' as the female parent and 'A110' as the pollen parent. These two selections are not commercially available and are not known by any synonyms. The new Scaevola plant was selected as a flowering plant within the progeny of this cross in a controlled environment in Enkhuizen, Netherlands. Plants of the new Scaevola have white flowers whereas plants of the unidentified selections have lavender blue flowers which is typical for the species *Scaevola aemula.* In addition, plants of the new Scaevola have, (contrary to the female parent which is slightly red), light green leaves, because of the lack of anthocyanin in the plant.

The new Scaevola plant has been asexually reproduced by cuttings in Enkhuizen, Netherlands and Sarrians, France over a two year period. It has been found to retain its distinctive characters through successive propagations, and this novelty appears to be firmly fixed.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Scawihatis' which distinguish 'Scawihatis' as a new and distinct cultivar:

1. Low-growing, spreading and cascading growth habit.
2. Medium internodes, dense and bushy plant form and freely branching plant habit.
3. Very freely flowering, more than 600 flowers and flower buds per plant.
4. Unique very large white fan-shaped flowers with light green-yellow eye.

DESCRIPTION OF THE DRAWING

This new Scaevola plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed observations set forth the distinctive characteristics of this new Scaevola plant. The data which defines these characteristics were collected from asexual reproductions carried out in Enkhuizen, Netherlands. The plant history was taken on 16 weeks old plants, blossomed under natural light in a greenhouse. The greenhouse conditions were as follows: daylength from 13 to 15 hours per day, temperature day 22 Celsius, temperature night 16 Celsius.

Color references are made to The Royal Horticultural Society Colour Chart of The Royal Horticultural Society of London.

| | Differences between the new cultivar 'Scawihatis,' its parents and a similar cultivar | | | |
|---|---|---|---|---|
| | 'Scawihatis' | 'A102' | 'A110' | 'White Champ' (U.S. Plant Pat. No. 12,027) |
| Flower color | White 155C lighter | Blue 98C | Blue 101C | White 157D |
| Flower size: | | | | |
| Length | Short to medium 2.6 to 2.8 cm | Medium 3.0 to 3.2 cm | Long 3.6 to 3.8 cm | Very short 2.0 to 2.2 cm |
| Width | Medium 2.8 to 3.0 cm | Medium 2.2 to 2.4 cm | Broad 2.8 to 3.0 cm | Narrow 1.6 to 1.8 cm |
| Size of the eye zone | Medium 0.5 cm | No eye 0 cm | Small 0.3 cm | Very small to small 0.1 to 0.2 cm |
| Shoot length | Short to medium 30 to 45 cm | Long 50 to 70 cm | Very long 60 to 80 cm | Very short to short 20 to 25 cm |
| Seedset | abundant | scarse | no | no |

The plant:

*Classification.*—Botanical — *Scaevola aemula.*

Parentage:

*Female parent.*—A seedling named 'A102' is one of our seedlings from our A-generation of plants bred in 1998.

*Male parent.*—A seedling named 'A110' is one of our seedlings from our A-generation of plants bred in 1998.

Propagation:

*Type cutting.*—Terminal cuttings.

*Time to initiate roots* (*summer*).—About 14 to 20 days at 24 degrees C.

*Time to develop roots* (*summer*).—About 25 days at 24 degrees C.

*Root description.*—Numerous, fine, freely branching.

Plant description:

*Plant form and growth habit.*—Semi-erect later spreading.

*Plant height*—About 24 cm.

*Plant width* (*spread*).—About 52 cm.

*Branching character.*—Freely branching and lateral branching at every node.

*Quality of branches.*—20 to 30 per plant.

*Blooming period.*—From May till November.

The stem:

*Diameter.*—2–3 cm.

*Shape.*—Round.

*Color.*—141B.

*Anthocyan pigmentation.*—Absent.

*Length of internode.*—2.8–4.2 cm.

*Texture.*—Smooth, no pubescence.

The foliage:

*Phyllotaxis.*—Alternate, single.

*Shape of blade.*—Oblanceolate.

*Texture.*—Upper side: Smooth. Lower side: Smooth.

*Anthocyanin pigmentation.*—Absent.

*Attachment to leaf.*—Petiolate.

*Venation.*—Pinnate.

*Leaf margin.*—Dentate.

*Leaf base.*—Attentuate.

*Leaf apex.*—Acuminate to apiculate.

*Length.*—Gradual size reduction towards lateral branch apex until leaves subtending flowers appear bract-like.

*Length.*—Lower leaves: 3.7–4.3 cm. Higher leaves: 1.1–1.4 cm.

*Width.*—Lower leaves: 1.8–2.4 cm. Higher leaves: 0.2–0.4 cm.

*Depth of incision.*—0.2 to 0.4 cm.

*Color.*—Upper side: 136A. Lower side: 137C.

*Petiole.*—No petiole existing.

The bud:

*Peduncle.*—No peduncle existing.

*Size of the bud.*—Length: 1.8–2.2 cm. Diameter: 0.2 cm.

*Shape.*—Lanceolate. Apex: Attenuate. Base: Acute.

*Anthocyanin pigmentation.*—Absent.

*Color.*—N144D.

*Sepals.*—Color — Base: N144C. Apex: 143A. Form: Opposite. Number: 2, parted. Size.— Length: 0.7 cm. Width: 0.15 cm. Shape: Ligulate. Margin: Entire. Texture: Smooth.

The flower:

*Form.*—Zygomorphic, semi-circular, fan-shaped with five petals fused at the base to form a tubular flower throat. Flower throat open along the upper surface exposing reproductive organs.

*Flower width.*—2.8–3.0 cm.

*Flower length.*—2.6–2.8 cm.

*Flower aspect.*—Horizontal to stem.

*Flower arrangement.*—Solitary, one flower per leaf axil, flowers sessile.

*Color.*—Upper side: 155C, even much lighter. Lower side: 155C. Middle stripe upper side: 155B. Middle stripe lower side: 155D.

*Color of the eye.*—150B.

*Size of the eye.*—0.5 cm.

*Perianth.*—Aspect: Fan-shaped, flat. Length, fan: About 2.7 cm. Width, fan: About 2.9 cm. Height: About 2 cm.

*Overlapping of the petals.*—Almost separate, fused at the base.

*Number of petals.*—Five.

*Shape of the petals.*—Oblanceolate.

*Apex.*—Mucronate.

*Margin.*—Entire.

*Surface texture.*—Smooth.

*Size.*—Width: 0.4 cm. Length: 1.5 cm.

*Number of flowers per lateral branch.*—60–80.

*Number of flowers at one time open.*—6–7.

*Fragrance.*—No fragrance.

*Lastingness of the individual flower.*—3–4 days.

*Lastingness of the bloom.*—New flowers continue to open in one branch for 30 days.

The reproductive organs:

*Androecium.*—Stamen number: Five. Anther shape: Oblong. Anther length: 1–2 mm. Anther diameter: Less than 1 mm. Anther color: 165A. Amount of pollen: Normal. Pollen color: 165A.

*Gynoecium.*—Pistil number 1. Pistil length: 1–1.4 cm. Style length: 0.8 cm. Style color: 144C. Stigma color: 144C. Stigma shape: Oblong. Ovary color: 144C.

The seed: From one flower one seed is formed, with one embryo within. Seedset is abundant in later season. From every flower one seed is produced. The seed is hardcoated, so little germination occurs without scarification.

*Size.*—Length: 1.5–2 mm. Width: 1 mm.

*Texture of the surface*—Smooth.

*Color when fallen from plant.*—146D.

*Color when ripe.*—166C.

Physiological and ecological characteristics: Good tolerance to heat. No resistance to pests and diseases common to Scaevola (mainly Verticillium and Phtophtora) is observed.

What is claimed is:

1. A new and distinct variety of Scaevola plant, substantially as herein illustrated and described.

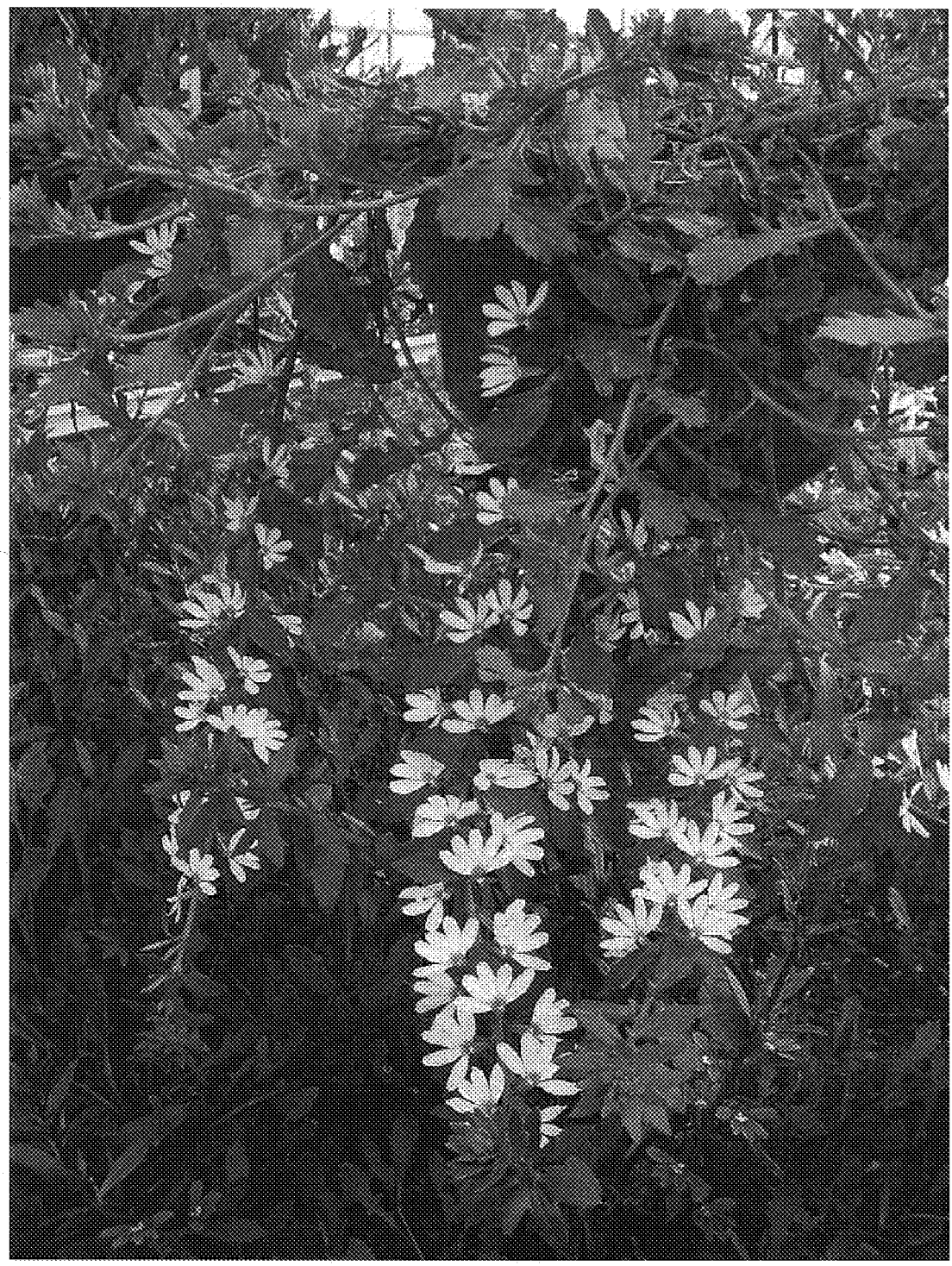

* * * * *